(12) United States Patent
Moos et al.

(10) Patent No.: US 6,634,212 B2
(45) Date of Patent: Oct. 21, 2003

(54) HIGH TEMPERATURE SENSOR

(75) Inventors: Ralf Moos, Friedrichshafen (DE); Thomas Birkhofer, Immenstaad (DE); Werner Maunz, Markdorf (DE); Ralf Muller, Deggenhausertal (DE); Willi Muller, Salem (DE); Carsten Plog, Markdorf (DE)

(73) Assignee: DaimlerChrysler AG (DE)

( * ) Notice: Subject to any disclaimer, the term of this patent is extended or adjusted under 35 U.S.C. 154(b) by 26 days.

(21) Appl. No.: 09/896,286

(22) Filed: Jun. 29, 2001

(65) Prior Publication Data
US 2002/0014107 A1 Feb. 7, 2002

(30) Foreign Application Priority Data

Jun. 30, 2000 (DE) .......................... 100 31 976

(51) Int. Cl.$^7$ .............................. G01N 7/00; G01N 9/00
(52) U.S. Cl. ................. 73/31.05; 73/23.2; 73/23.31
(58) Field of Search ............................. 73/23.2, 23.31, 73/31.05, 31.06

(56) References Cited

U.S. PATENT DOCUMENTS

| 5,143,696 | A | * | 9/1992 | Haas et al. | 422/90 |
|---|---|---|---|---|---|
| 5,522,980 | A | * | 6/1996 | Hobbs et al. | 422/88 |
| 5,756,879 | A | * | 5/1998 | Yamagishi et al. | 73/23.31 |
| 5,918,261 | A | * | 6/1999 | Williams et al. | 73/31.06 |
| 5,928,609 | A | * | 7/1999 | Gibson et al. | 73/23.34 |
| 5,965,451 | A | * | 10/1999 | Plog et al. | 422/98 |
| 6,069,013 | A | * | 5/2000 | Plog et al. | 422/98 |
| 6,134,946 | A | * | 10/2000 | Liu et al. | 73/31.06 |
| 6,173,602 | B1 | * | 1/2001 | Moseley | 73/31.06 |

* cited by examiner

Primary Examiner—Daniel S. Larkin
(74) Attorney, Agent, or Firm—Pendorf & Cutliff

(57) ABSTRACT

High temperature substance sensor, including
 a substrate (4),
 a device (6) for raising and maintaining the temperature of the sensor, and
 a layer like capacitor structure (38) with structure sizes smaller than 50 $\mu$m, upon which a functional layer (18) is applied.

In accordance with the invention the layer-like capacitor structure (38) is produced by the following:
 application of a complete or already pre-structured electrically conductive layer as precursor of the capacitor structure (38) using a thick layer technique,
 structuring the electrically conductive layer using a photolithographic structuring process.

5 Claims, 18 Drawing Sheets

HIGH TEMPERATURE SENSOR

BACKGROUND OF THE INVENTION

1. Field of the Invention

The invention concerns a high temperature sensor, particularly an exhaust gas sensor in the exhaust line of an automobile.

2. Description of the Related Art

In order to meet the ever more stringent governmental requirements with respect to air quality, very selective gas sensors are necessary. Such sensors can be employed for example for monitoring pollutant levels, or to activate an alarm when a threshold concentration of a dangerous or poisonous gas in the environmental atmosphere has been exceeded. It is also possible to employ such gas sensors directly in the exhaust gas of an internal combustion process. Examples thereof include selective hydrocarbon sensors such as known for example from EP 0 426 989 or selective ammonia sensors as known for example from DE 197 03 796.

The mentioned examples concern gas sensors produced using planar technology (and in particular thick layer technology or thin layer technology). In FIG. 1 various views of the typical design of such a sensor are schematically illustrated. A substrate 4 has provided on the sensor lower side a structure 6 for heating and eventually temperature measurement, and has provided on the sensor upper side at the sensor tip a capacitor structure. This structure, which is again shown in FIG. 2 in enlarged representation, is comprised of a plurality of staggered or offset electrodes 8 which are alternatingly connected to conductor line 10 or conductor line 12. The conductors 10 and 12 have respective contact pads 14 and 16 on the sensor connection side, onto which connector wires are applied. If an alternating current is applied to the two conductors, then the capacitates $C_L$ of this structure (referred to in the following as empty capacity) can be measured. Since this capacitor structure looks similar to inter-digitating fingers, such a structure is referred to also as interdigitatec capacitor (IDC). If now upon this IDC structure a functional layer 18—not shown for purposes of better understanding—is applied, of which the electrical characteristic changes upon exposure to a gas, then one can construct therewith a gas sensor. Such a construction is in principle not only suitable for sensors which detect components of a gas mixture, but rather also for all chemical or substance sensors.

The term "substance sensor" is intended herein to mean a sensor for determination of concentrations of a substance in a substance mixture, that is, for example, a sensor for determining the concentration of a component of a gas mixture or a sensor for determining a component of a fluid or a sensor which changes its output signal on the basis of an interaction with a gas or a fluid.

The above described arrangement comprised of substrate, heating and/or temperature measurement resistor device, and IDC structure will in the following be referred to as "U-carrier". A sensor in this respect is also comprised of at least a transducer and a functional layer.

Estimation of Signal Size

The signal change to be measured depends upon the geometry of the IDC structure. This is shown again in FIG. 2 in enlarged view. The entire IDC structure has as external dimensions the length L and the breadth B. Across the breadth B electrode fingers of the breadth b are provided in separation s. One can therewith imagine the entire capacitor as a parallel circuit (electrically switched in parallel) comprised of multiple component capacitors, wherein each partial capacitor is comprised of two adjacent fingers. The empty capacity of these partial capacitors, and therewith also the total empty capacity $C_L$, increases with the finger length L. With a reduction in the finger separation s the empty capacity of the partial capacitors likewise increases, since the density of the field line or line of electric flux between two fingers increases (in comparison: in plate capacitors the capacity is inversely proportional to plate separation). Since the total capacity is based upon the parallel circuitry of the partial capacities, the total capacity is the larger the greater the number of partial capacitors which can be provided within the breadth B with decreasing finger breadth b, thus the capacity of the total capacitor increases, since the number of the parallel switched partial capacitors increases with decreasing finger breadth b at constant outer dimension B. With decreasing finger spacing s in accordance therewith, the capacity of the total condenser even increases over-proportionally (almost quadratically), since on the one hand the number of the partial condensers and on the other hand their capacity increases.

The height of the electrode (layer thickness) is only of minimal consequence.

In the following, a few theoretical calculations of the total capacity $C_L$ will be presented, which are carried out using a finite element method. Therein, the measurements of a typical IDC structure, that is, approximately 5 mm×6 mm (L×B), is used as basis. For the relative dielectric constant, $\in_r$ was presumed to have a value of $\in_r \approx 10$ as disclosed in published literature as conventional for $Al_2O_3$ substrates. The results of the calculations confirm that the layer thickness of the IDC structures can be disregarded.

It has further been determined, as best seen in FIG. 3, that an optimal relationship of line separation s and finger breadth b of $s/b \approx 2$ exists, at which the total empty capacity $C_L$ reaches a maximum. In FIG. 3, a finger separation of $s=20$ μm was presumed. At a finger breadth of $b=9.88$ μm, there is the maximum empty capacity. If one varies the finger separation s, then one can determine that the value of the optimal relationship is almost independent of the separation of the fingers. One achieves for example at $s=20$ μm an optimal value for the finger breadth of $b=9.88$ μm ($s/b=2.024$) and at $s=10$ μm an optimal finger breadth of $b=0.54$ μm ($s/b=1.203$).

The optimal empty capacity for finger separations ranging from 10 μm to 30 μm is shown in FIG. 4. One can recognize that at a finger separation of approximately 20 μm, a total empty capacity $C_L$ of almost 40 pF can be achieved. Table 1 clearly shows the relationship between the geometric size b and s and the total empty capacity $C_L$. At structure breadths for s and b of approximately 100 μm, one achieves only a total empty capacity of $C_L < 10$ pF.

TABLE 1

| Finger Separation s/μm | Optimal Finger Separation b/μm | Total Empty Capacity $C_L$/pF | Maximal Capacity Change $\Delta C_{max}$/pF |
| --- | --- | --- | --- |
| 10 | 4.54 | 82.33 | 4.12 |
| 15 | 7.22 | 53.22 | 2.66 |
| 20 | 9.88 | 39.28 | 1.96 |
| 25 | 12.53 | 31.10 | 1.56 |
| 30 | 15.15 | 25.73 | 1.29 |

If one next applies the functional layer 18, then the measurable capacity increases, depending upon the dielectric constant $\epsilon_r$ of the functional layer and its thickness. It can however be shown that the influence of the layer thickness of the functional layer in particular at values of the dielectric constant $\epsilon_r$<5 hardly plays any roll. If one presumes that the supplemental capacity, which is attributable to the functional layer, corresponds to the half value of the empty capacity, and if one further presumes that the supplemental capacity during gas sampling changes at a maximal of 10% of its value, then one obtains the maximal capacity change $\Delta C_{max}$ to be measured, which is entered in the fourth column of Table 1. It is immediately evident from Table 1 that one, in order to even be able to make reliable measurements, must have as small as possible finger breadth b and finger separation s. This is in particular then the case, when long conductors or lead lines, which conventionally exhibit capacities of a few pF/m, are required. This is for example the case, when the sensor is to be employed in the exhaust gas stream of an automobile, in order to be able to measure the ammonia or hydrocarbon content in the exhaust gas of an automobile. Therein, it is to be observed, that even this lead line or conductor capacity is conventionally not constant, but rather changes with the environmental temperature. This conductor capacity can only be compensated for in complex or expensive manner.

Further complicating matters is that small measurement currents are used. Thus, one calculates at an alternating voltage amplitude of 1 V and a capacity of 50 pF at a measurement frequency of 1 kHz a capacitive current of 314 nA, wherein the maximal signal change (that is, the measurement effect), however, only corresponds to approximately 16 nA. If one wants to resolve the sensor signal to 1%, then a measuring current of 160 pA must be resolved. Since the measuring current in a capacitive system with constant applied measurement voltage amplitude increases with increasing frequency, then one should measure at higher frequencies, which however may bring about a danger of intensified stray effect and electromagnetic interference. Since with a given measurement voltage the measurement current is proportional to the capacity, this is a further reason to select as fine as possible structures, that is, high capacity for the IDC structure.

The above discussed range of problems for functional layers, of which the capacitive characteristics change upon exposure to or interaction with gas, applies in appropriate manner also for sensors of which complex impedance (complex alternating current resistance) changes with gas sampling. Above all, high ohm functional layers, which provide only small capacitive values, require a fine as possible structure.

As a structure breadth which provides signals which are just barely detectable with economically justifiable measurement technology and subsequently electrically processable, 50 µm has been found to be satisfactory.

Planar gas sensors can be produced either in accordance with the thick layer technique or the thin layer technique (typically processes of the thin layer technique: sputtering, vapor depositing, or CVD). Examples, in which also the processes are disclosed, which an be used for production of substance sensors in the thick layer technology, can be found in J. Gerblinger, M. Hausner, H. Meixner: Electric and Kinetic Properties of Screen-Printed Strontium Titanate Films at High Temperatures, J. Am. Cer. Soc., 78[6] 1451–1456 (1995) or M. Prudenziati (Editor): Thick Film Sensors, Particularly Section I: Thick Film Technology, pages 3–37, Elsevier-Verlag, 1994 or in DE 37 23 052. It is possible to combine thin layer techniques and thick layer techniques (so called hybrid technology), but this is expensive.

In the manufacturing of high temperature substance sensors, the following requirements are to be taken into consideration (the term high temperature sensors is understood to mean those sensors which are heated to temperatures above 300° C. This type of requirement is placed particularly upon exhaust gas sensors, for example in the exhaust gas of internal combustion engines in vehicles):

On the one hand, thin layer techniques make it possible to produce the finest structure breadths of as small as a few µm, which for the above mentioned example would be quite sufficient. However, thin layer processes only make possible layer thicknesses below 1 µm. In rough to abrasive environmental conditions, in particular with long operation at high temperatures, such thin layers are not sufficiently durable over time. Further, it is necessary, when using conventional high temperature stable electrode materials, such as gold or platinum, for the thin layers, so called adhesion promoters which for example could be a few nm thick layers of chrome or titanium. At the high temperatures at which high temperature gas sensors operate, for example exhaust gas sensors, these materials diffuse to the upper surface of the electrode and there react with the functional layer 18. This changes the functional layer, and the sensor can become desensitized to the gas to be detected. Besides this many functional layers, in particular zeolites or complexes of multi-oxides cannot be produced in the thin layer technique. Besides this one requires for the production of components in the thin layer technology normally specific or particular substrates with a very low surface roughness, which is substantially more expensive (by a factor of five to ten) than conventional ceramic substrates. Since most thin layer processes are vacuum processes, one requires for the thin layer techniques complex and expensive apparatus, which can generally be amortized only when producing large patches of pieces.

The above discussed arguments lead to the conclusion, that the thick layer technique would be the most suitable manufacturing process for high temperature gas sensors both for technical as well as cost reasons.

However, unfortunately, using the thick layer technique conventionally, the finest structure breadths that can be reproducibly produced are only in the range of 70 µm to 100 µm. The required resolution of below 50 µm, in particular approximately 20 µm, could not be achieved with the conventional thick layer techniques for gas sensors according to the state of the art.

It is thus the task of the invention to provide a high temperature substance sensor with structural sizes smaller than 50 µm, with which the described range of problems with respect to the manufacture of the sensor can be overcome.

SUMMARY OF THE INVENTION

In accordance with the invention, the production of the capacitor or capacitor structure of the high temperature substance sensor occurs from a combination of the thick layer technique process and a photolithographic structuring process, which is employed in the planar technique for production of semiconductor components. It is now for the first time employed in the manufacture of substance sensors. The production of the other layers of the high temperature substance sensors occurs advantageously using the thick layer technique, for example, with the silkscreen printing or stencil printing technique.

For the production of the capacitor structure, there is first produced, using the thick layer technique, a complete (closed) or already pre-structured capacitor layer as a precursor of the capacitor structure. Subsequently, there occurs the structuring of the capacitor layer using photolithography.

The inventive high temperature substance sensor is particularly suitable for employment has exhaust gas sensor in internal combustion exhausts, for example, in the exhaust of an automobile.

It can be constructed for example as an ammonia or hydrocarbon sensor.

BRIEF DESCRIPTION OF THE DRAWINGS

An example of the invention will be described with reference to Figures. There is shown.

DETAILED DESCRIPTION OF THE INVENTION

Figure 1:
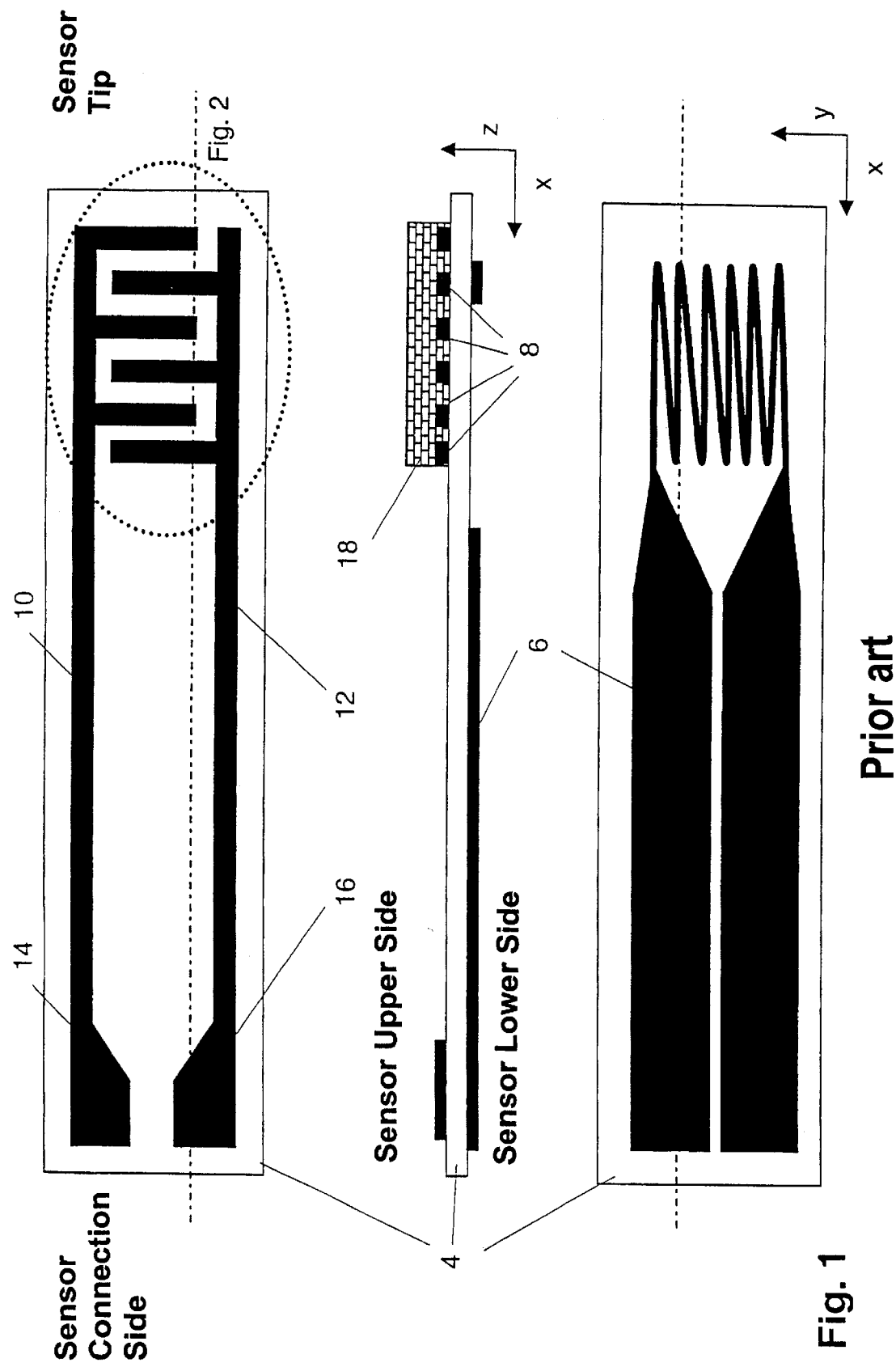
FIG. 1 the design of a substance sensor, with various views.
Figure 2:
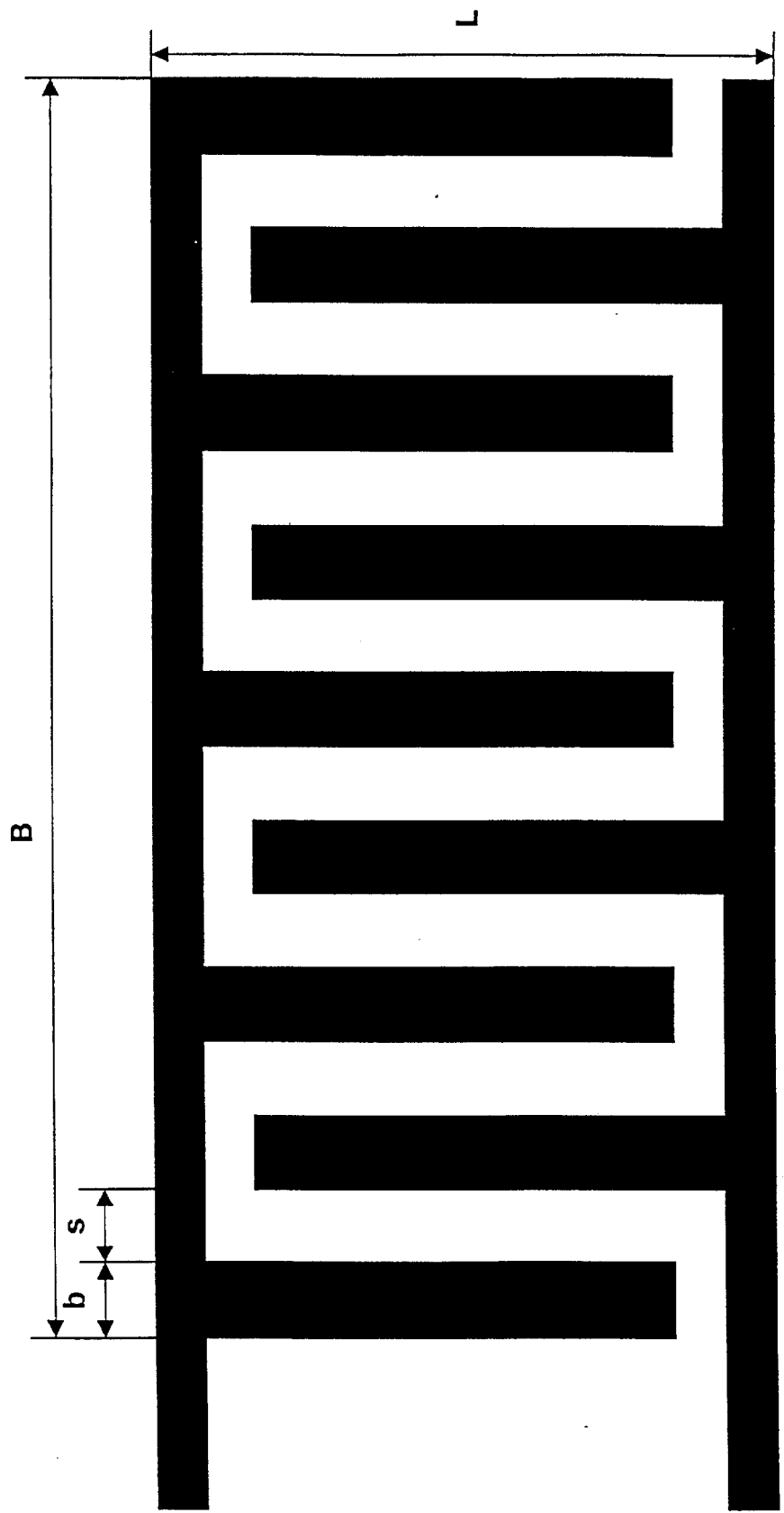
FIG. 2 the capacitor structure of a substance sensor.
Figure 3:
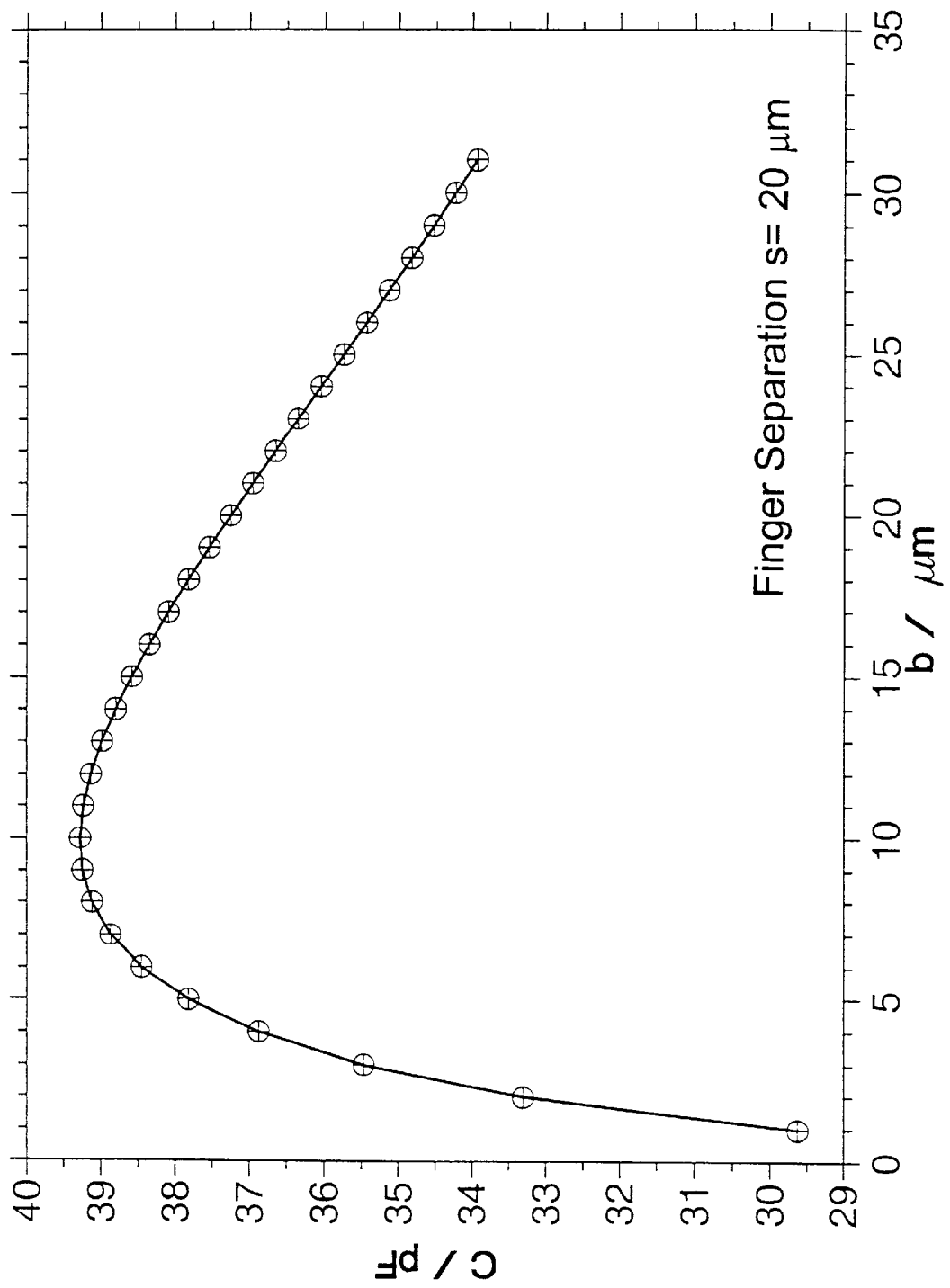
FIG. 3 the capacity C of an interdigitated capacitor structure depending upon the finger separation b with constant line separation s.
Figure 4:
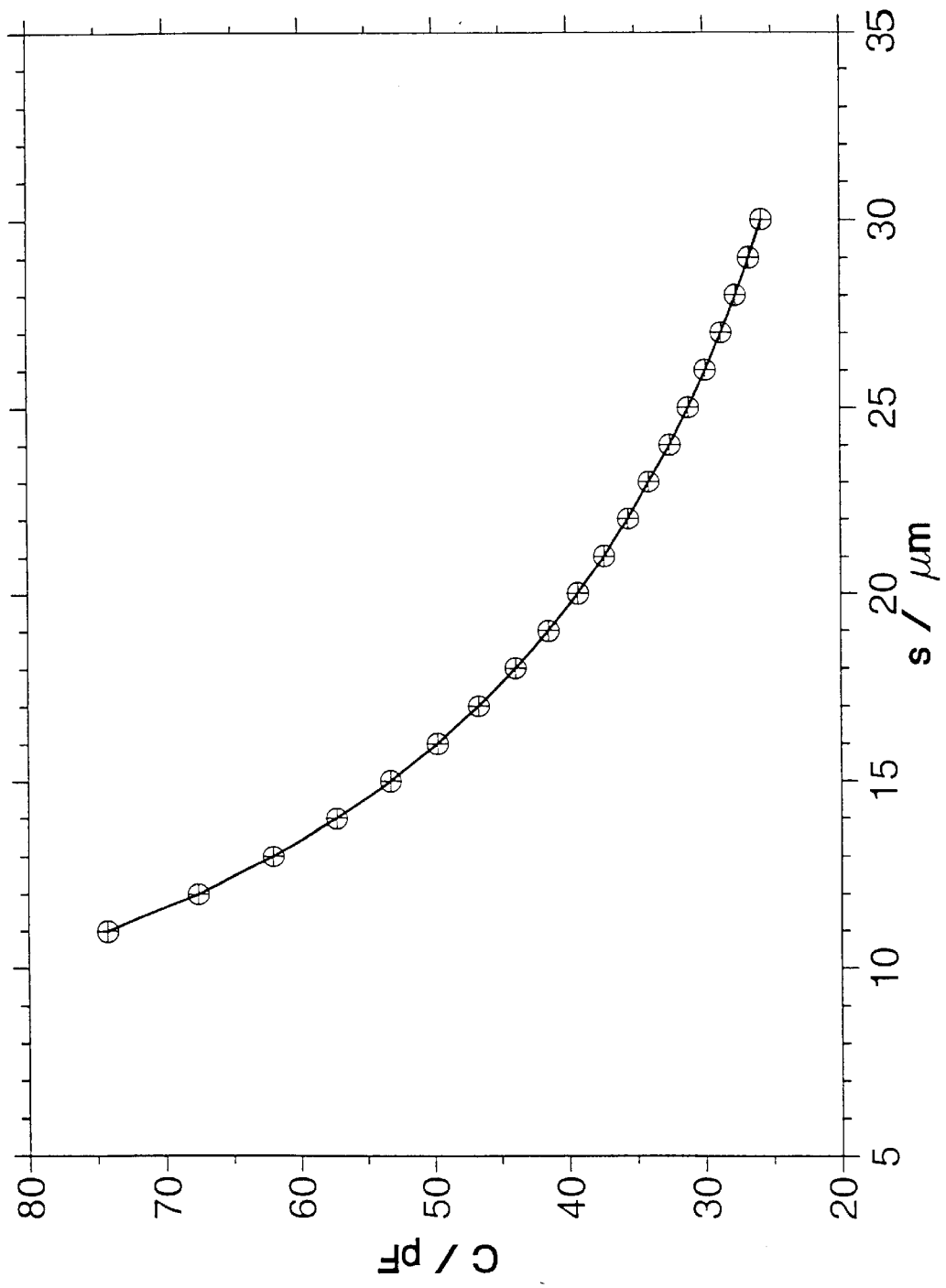
FIG. 4 the maximal capacity C of an interdigitated capacitor structure with variable finger separation b and constant line separation s for multiple values of the line separation s.
Figure 5A:
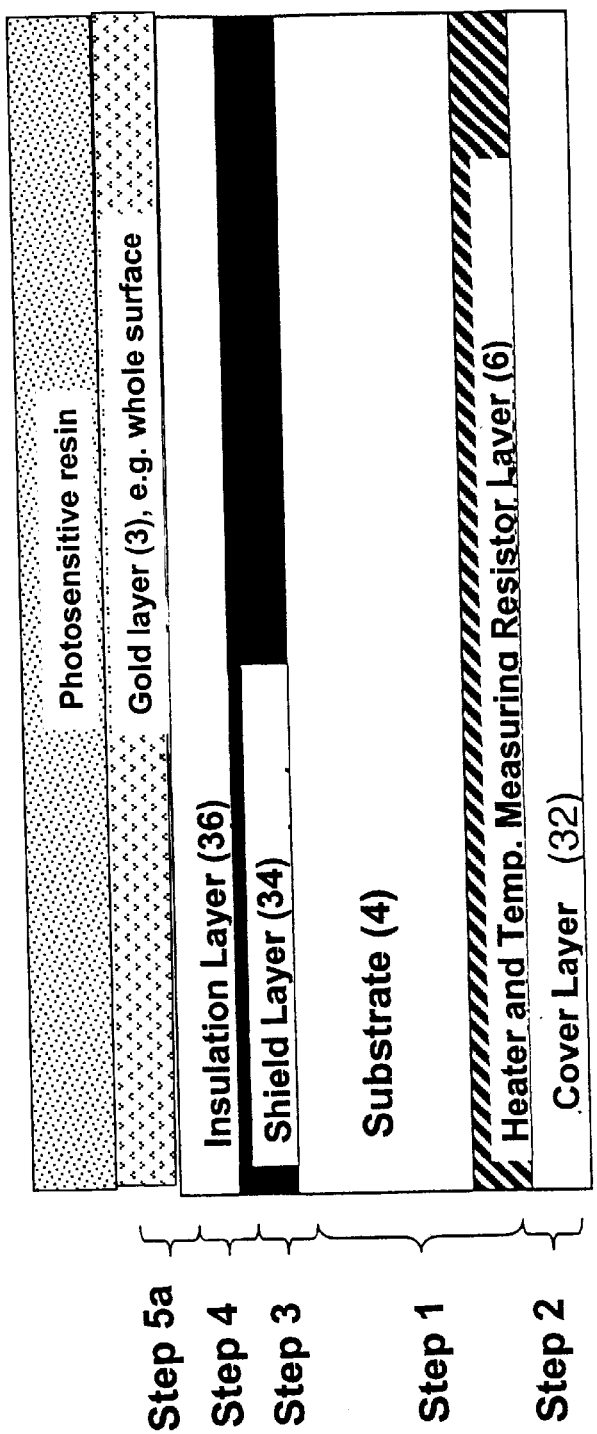
FIGS. 5,6 respectively diagrams illustrating the sequence for the manufacture of an inventive high temperature substance sensor.
Figure 5B:
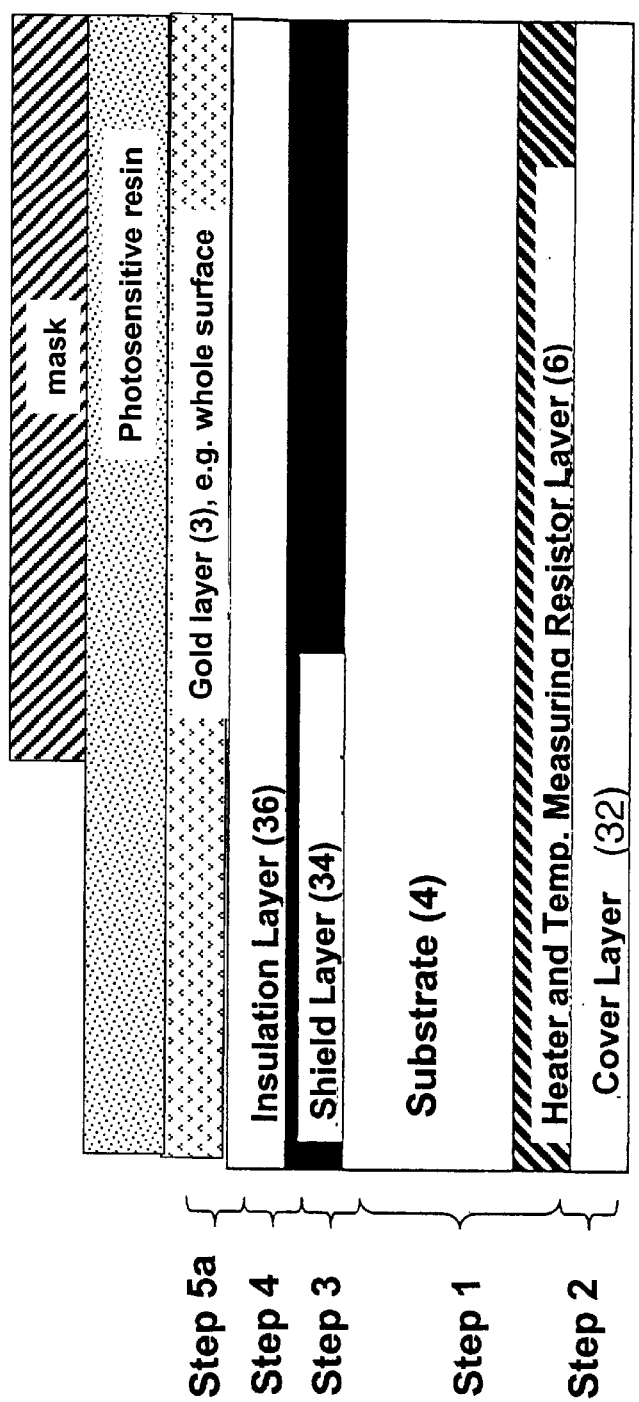
Figure 5C:
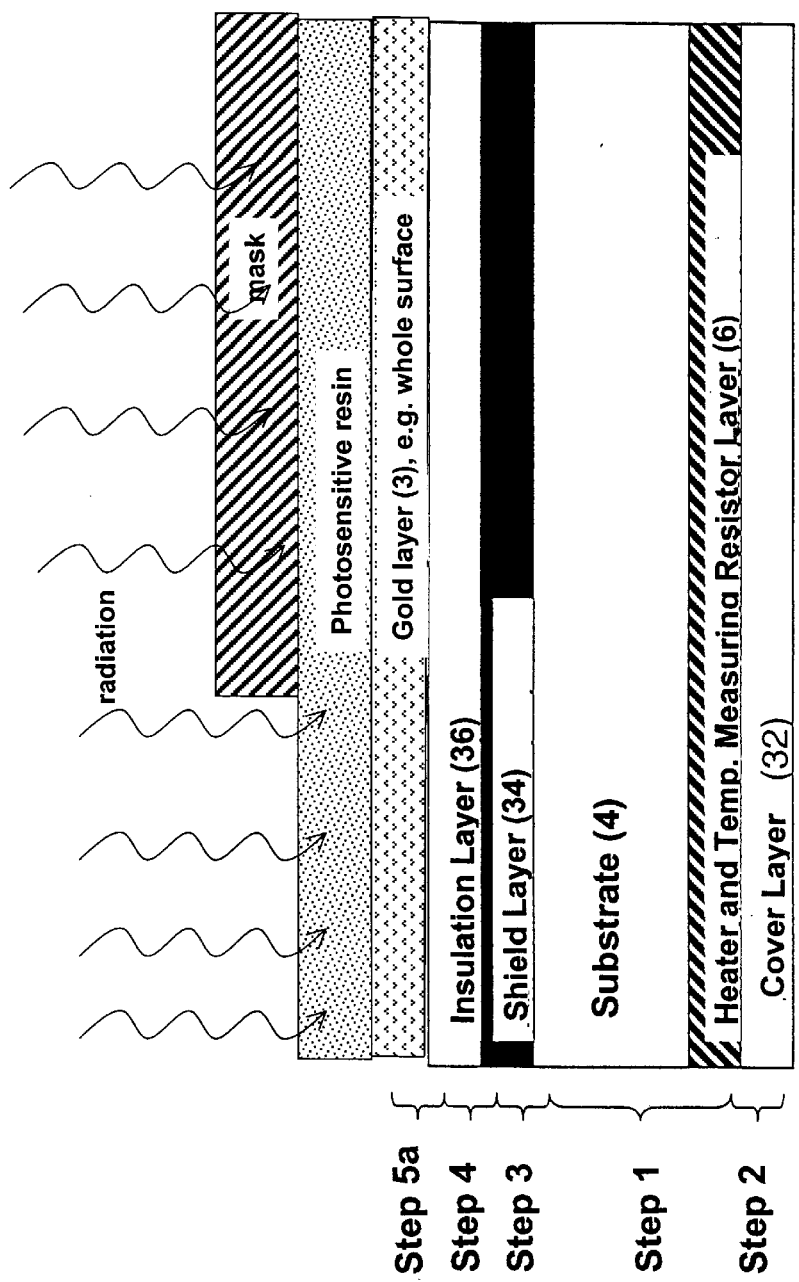
Figure 5D:
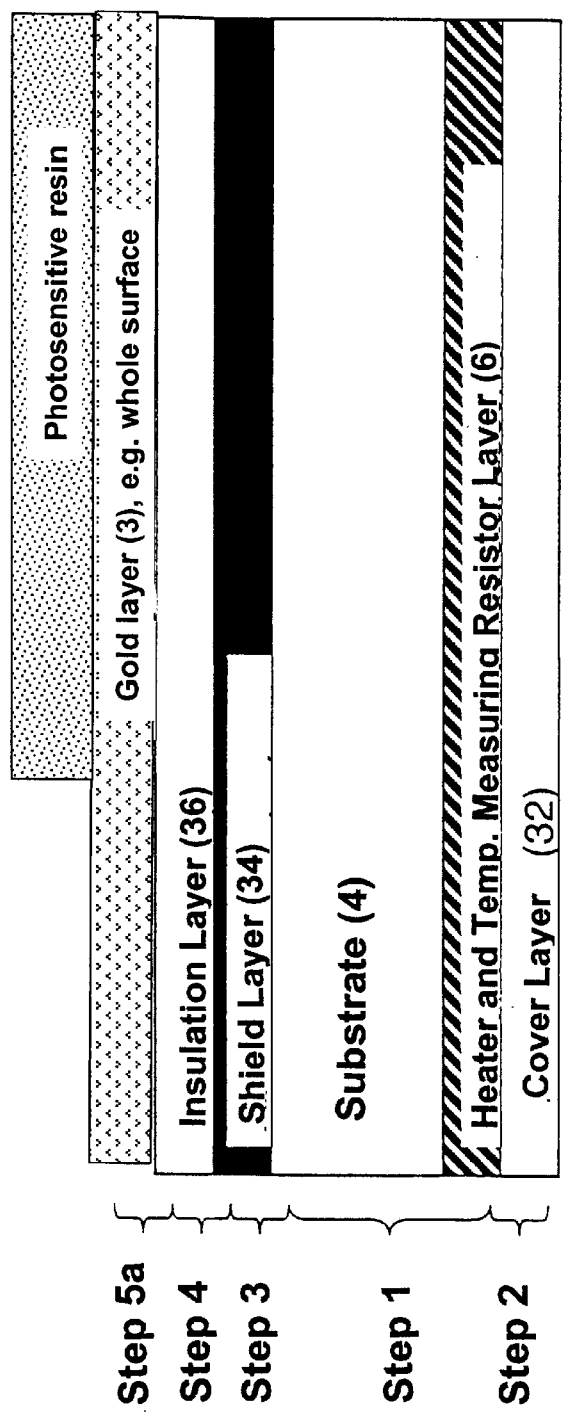
Figure 5E:
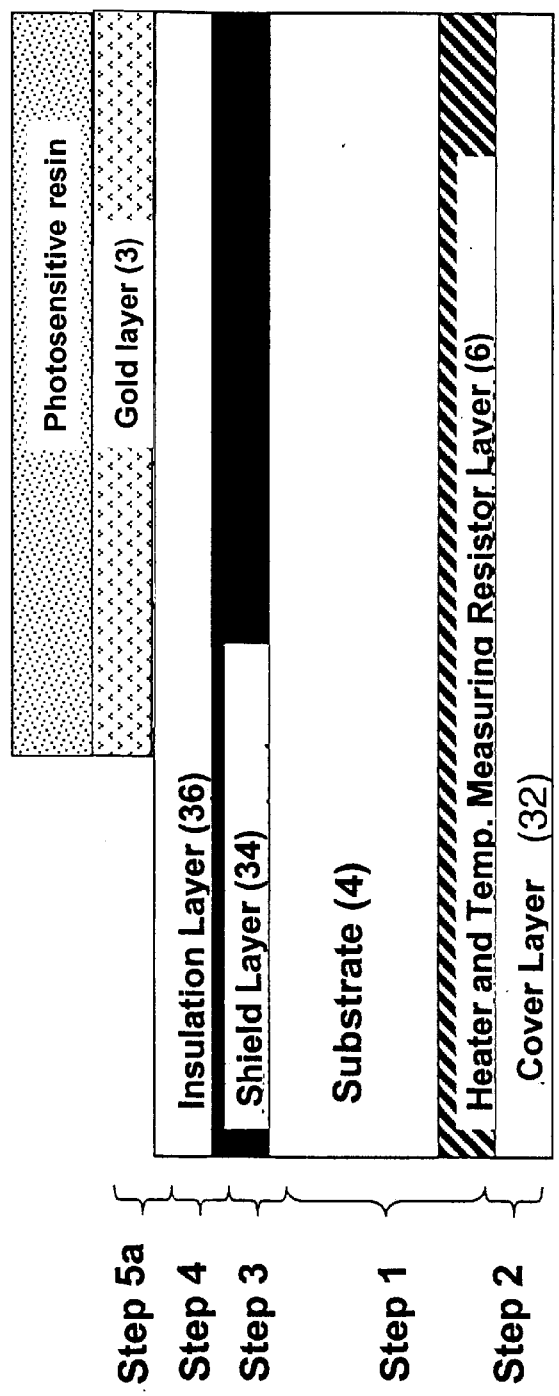
Figure 5F:
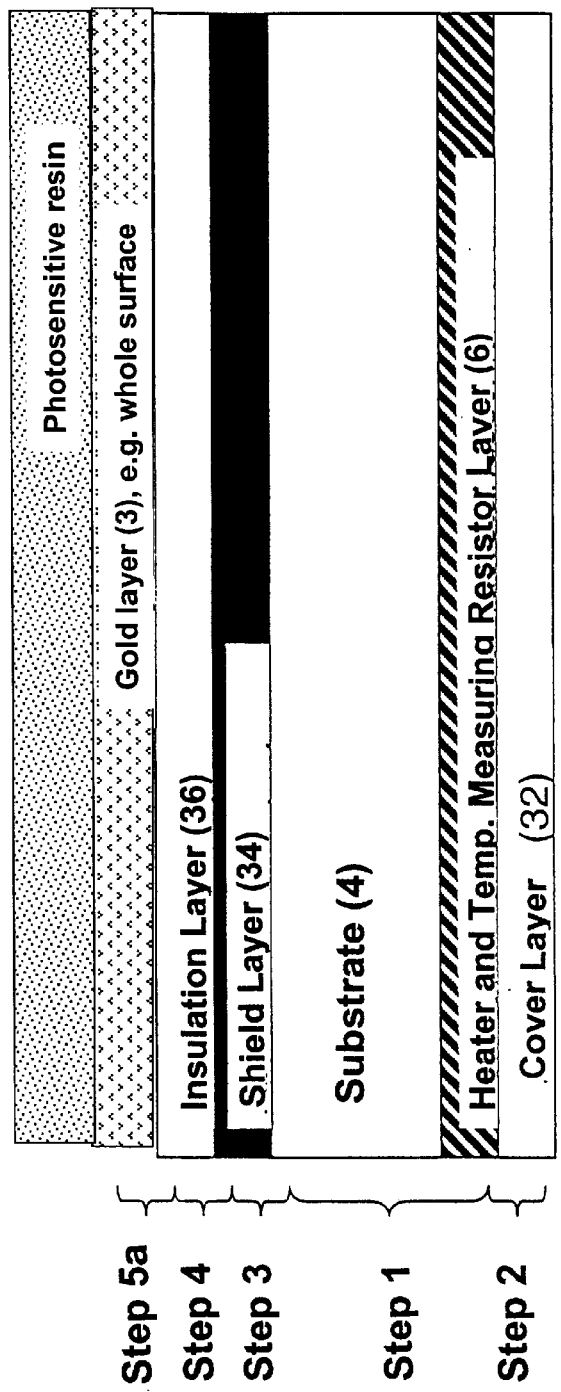
Figure 5G:
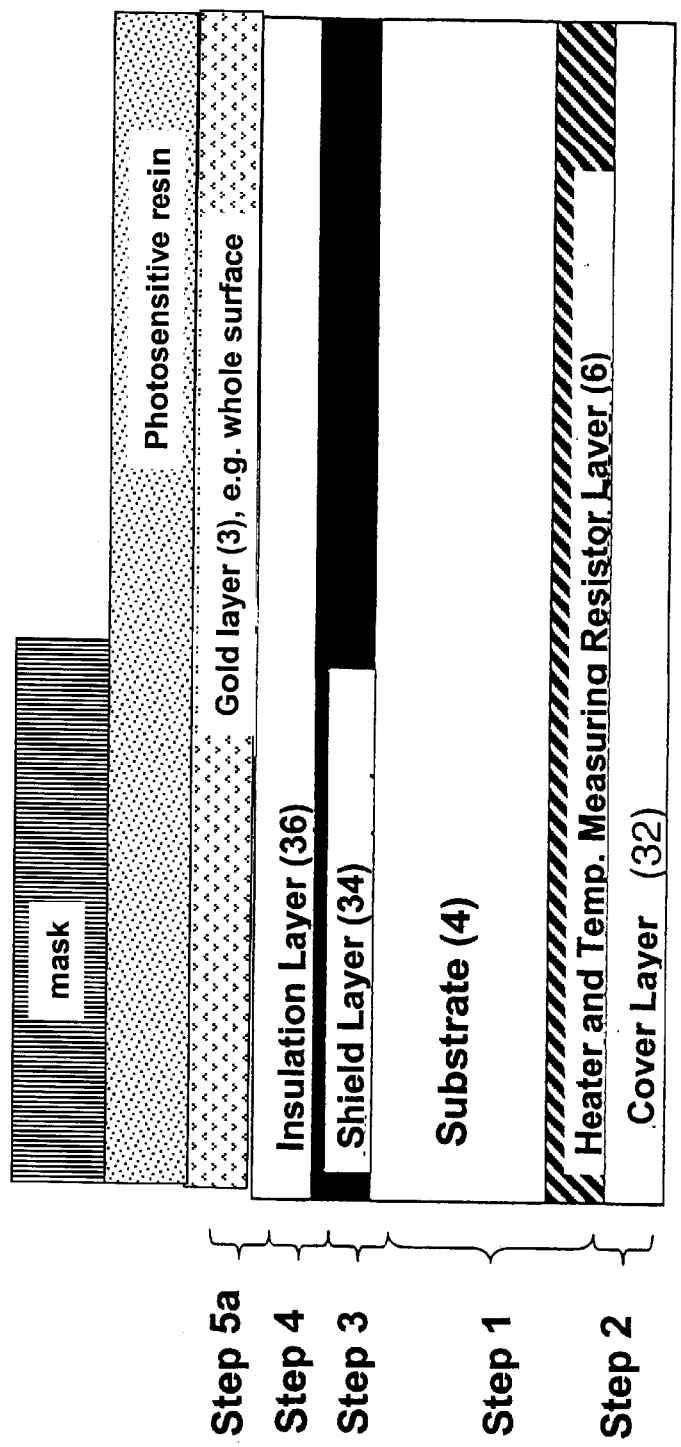
Figure 5H:
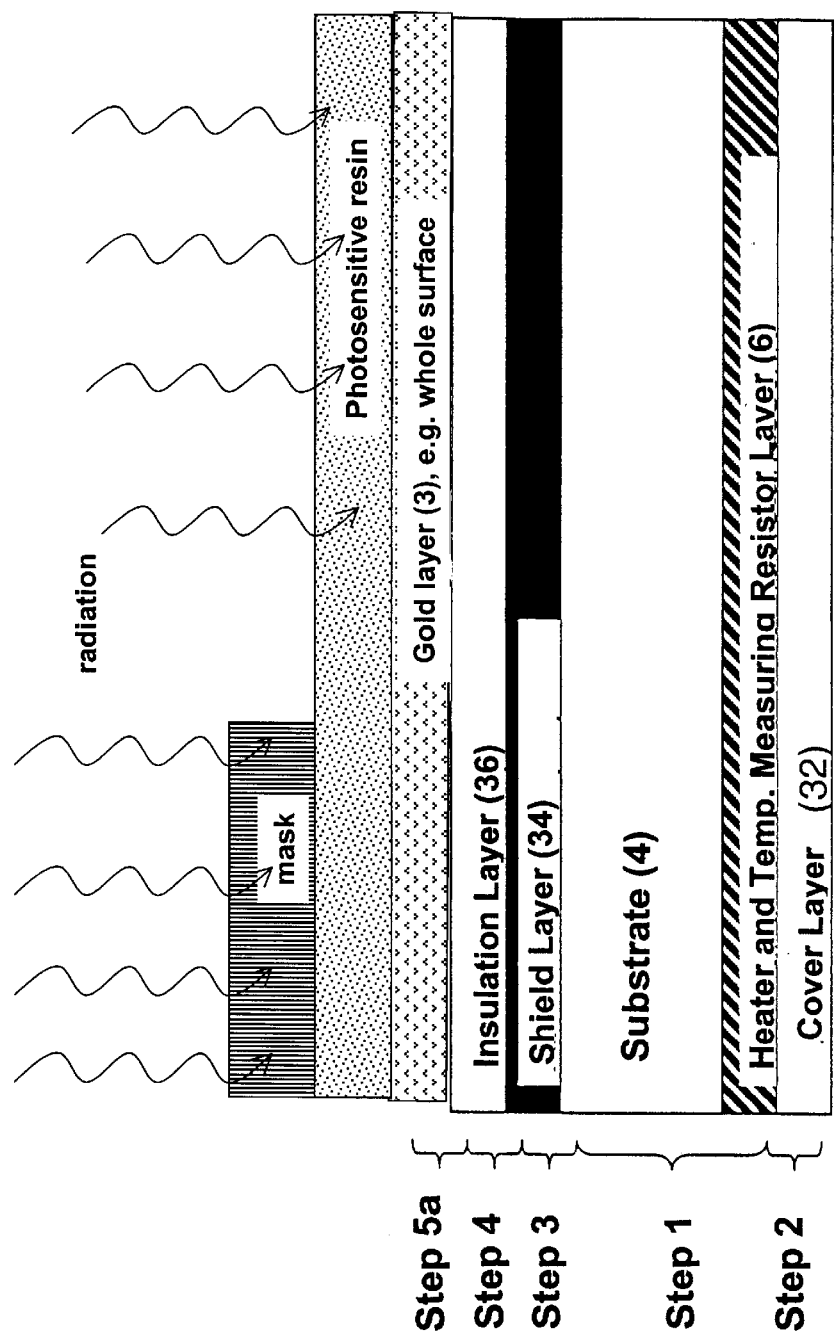
Figure 5I:
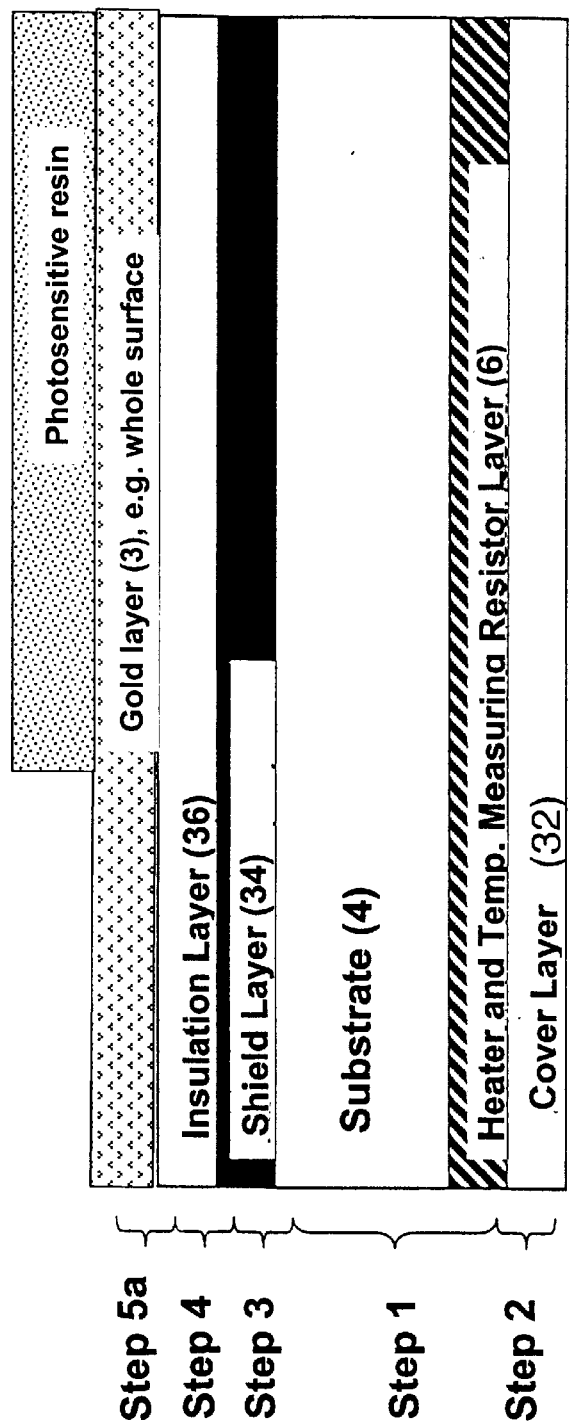
Figure 5J:
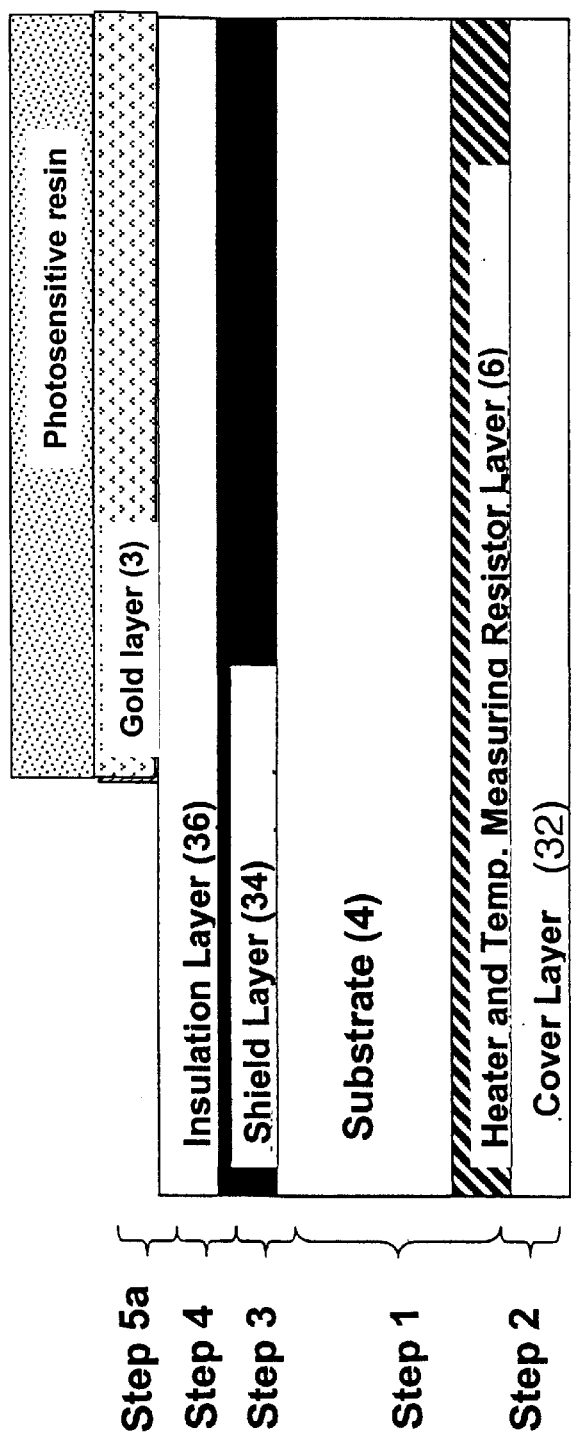
Figure 6:
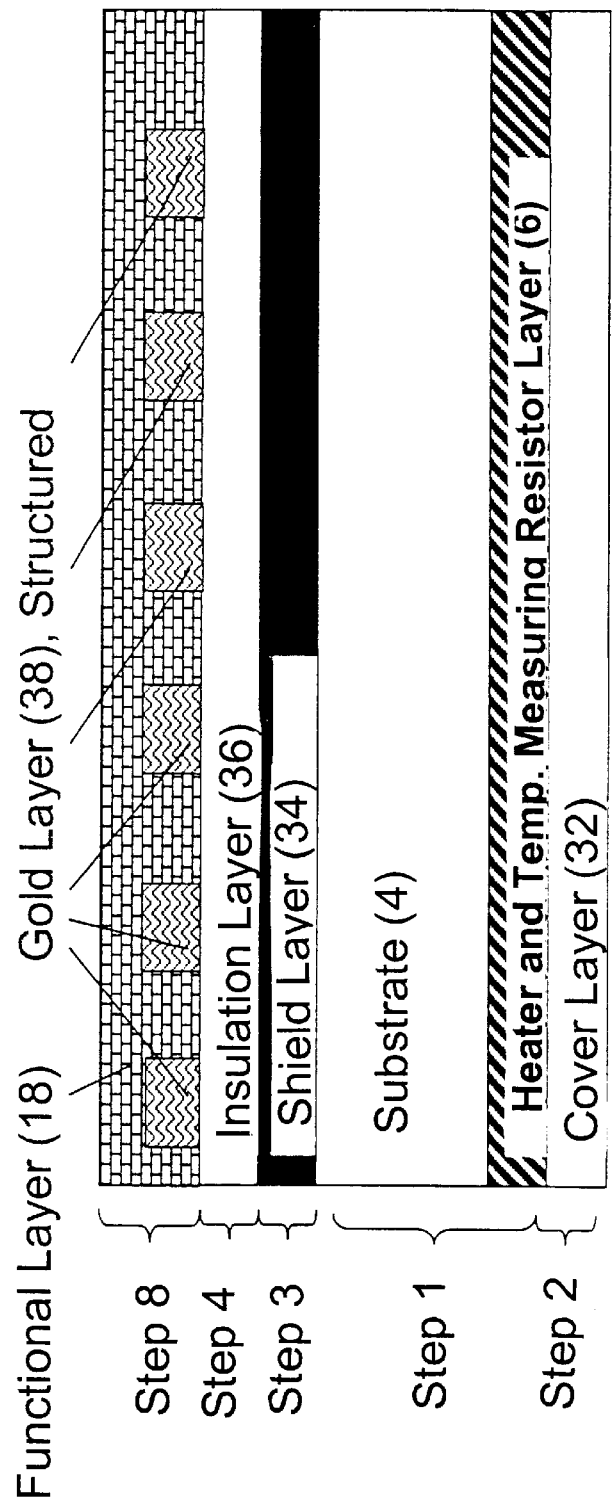

The production of the inventive high temperature sensor will be described step-by-step for a typical example and with reference to FIGS. 5 and 6.

Step 1

Upon a ceramic substrate 4, which is comprised for example of a conventional 96% $Al_2O_3$, there is applied on the lower side a structured heater and temperature measurement resistor structure 6, which can be comprised for example of platinum, and this is subsequently fired at 1400° C. The application of the heater and temperature measuring resistor structure 6 occurs using a silkscreen printing technique, as an example of a thick layer technique process.

Step 2

Upon this layer a ceramic cover layer 32, for protecting the heat and temperature measurement resistor structure 6, is applied over the entire surface using silkscreen printing and fired at, for example, 1300° C.

Step 3

Next, on the other side of the substrate a barrier layer 34, which can be comprised for example of platinum, having an appropriate structure is applied using silkscreen printing and fired at 1250° C.

Step 4

Upon the barrier layer 34 there is likewise applied using silkscreen printing a ceramic layer, glass layer, or a glass ceramic layer 36 for electrical insulation, and this is fired.

Steps 3 and 4 are only necessary when the gas sensor requires a layer for electrical insulation or shielding. This serves to shield the sensor measuring process against interferences on the basis of the heat process at the heat and temperature measurement resistor layer 6.

Step 5a

Next, by means of silkscreen printing, a gold layer 38 is applied either over the entire surface or already pre-structured, and fired.

Step 5b

Upon this gold layer 38, a photosensitive resin layer is applied by means of a spin coat process and is so heated, that the resin cross-links. A photo mask, which contains the IDC structure, is placed precisely upon the photo resin layer and the photo resin is illuminated or exposed to radiation. Subsequently, it is developed, whereby the illuminated parts of the resin can be removed in a suitable alkaline solvent. The resin part now remaining upon the gold layer 38 is an image of the IDC structure. In an etch bath, comprised for example of an iodide-potassium-iodide solution, the surfaces of the gold layer 38 not covered by the resin are removed. Subsequently, carefully, the rest of the etching solution must be removed using distilled water. Then, in a suitable solvent (for example acetone), the remainder of the resin layer is removed. Thereunder, now the IDC structure becomes visible, and once again is cleansed. In order to remove any possible present resin or solvent residues, the gold layer is once again fired for cleansing. It is also possible to bypass the step of removing the resin layer using the solvent by proceeding directly to the step of firing the resin. According to this process, the IDC structure is produced and now the functional layer can be applied. The structure is sketched in FIG. 6. The maximal achievable resolution was, in the framework of experiments, dependent upon the selection of the gold paste, determined to be approximately 15 $\mu$m. The work should be carried out in a clean room, since impurities can result immediately in a defect (short circuit or interruption) in the IDC structure. The employed gold paste should be so prepared or produced, that in the fired condition a flat as possible surface if produced, upon which the illumination or photo mask can be laid.

Step 5 is a combination of a process of the typical thick layer technique with a photolithographic process as employed in the planar technology for the manufacture of semiconductor components. It is now used for the first time for the manufacture of gas sensors. One obtains an IDC structure which exhibits all of the required characteristics for the production of high temperature gas sensors, such as layer thickness in the $\mu$m-range, temperature stability, and manufacturability on economical substrates as conventionally employed in the thick layer technology. In addition, such a transducer, however, also exhibits the above-described essential fine resolution. In the above Step 5, the manufacture of an IDC structure using a photolithographic structured gold layer is described. Such an IDC structure can be produced using platinum or other high temperature stable metals. In the case of platinum as the work material for the IDC, a suitable platinum layer is applied in the thick layer technology and this is structured using a suitable resin and a suitable solvent.

Alternatively to the described photolithographic structuring process, in which the applied photo mask corresponds to the capacitor structure, and in which in a further step the illuminated or irradiated area of the resin layer can be removed, also a process can be employed using the so-called negative resin. Therein, the applied photo mask corresponds to the negative of the capacitor structure, wherein in a further step the non-irradiated area of the resin layer is removed.

Step 6

Upon the completed transducers conductive strips 10 and 12 are printed using the silk printing technique and these are again fired in. The contact pads 14 and 16 can be thickened once again using, for example, silkscreen printing and firing of a suitable paste, so that they can make good contact with the connecting wires. The Step 6 is not shown in FIG. 6 for reasons of easier understanding of the figures.

Step 7

It could in certain cases be advantageous to print upon the lead lines a protective layer and to subsequently fire the protective layer. With Step 6 or Step 7, the transducer is completed. Step 7 is omitted from FIG. 6 for easier overview.

Step 8

On the transducer, there is now applied the functional layer 18 likewise using the thick layer technique and fired.

The advantages of this inventive construction are once again elucidated on the basis of the following example. As example for a typical functional layer, a zeolite layer is employed which can be used for a selective ammonia sensor for application in the exhaust gas flow of an automobile.

Figure 7:
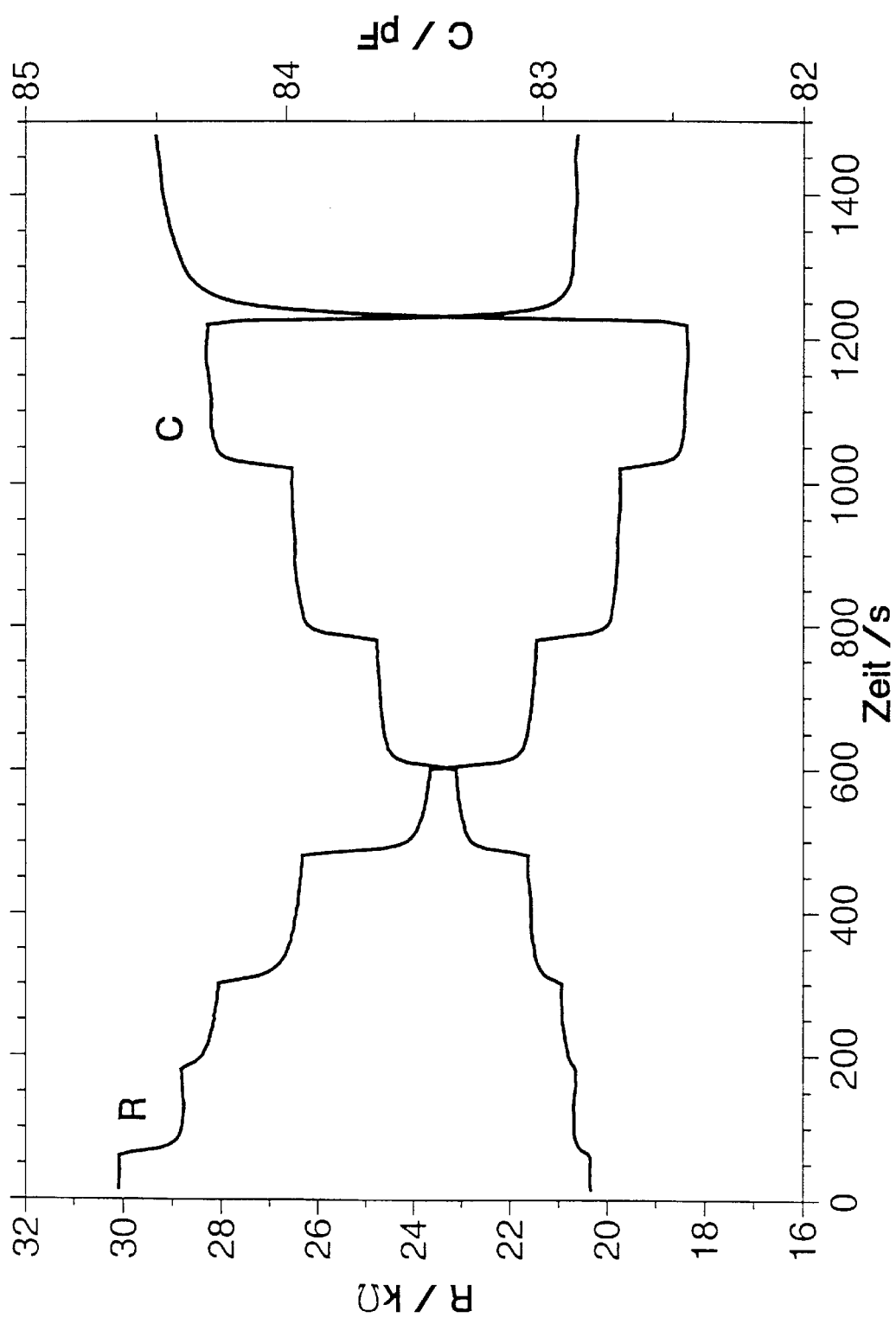
FIG. 7 measurement protocol, obtained using a substance sensor produced using a hybrid technique, of which the finger breadth s=10 $\mu$m.
Figure 8:
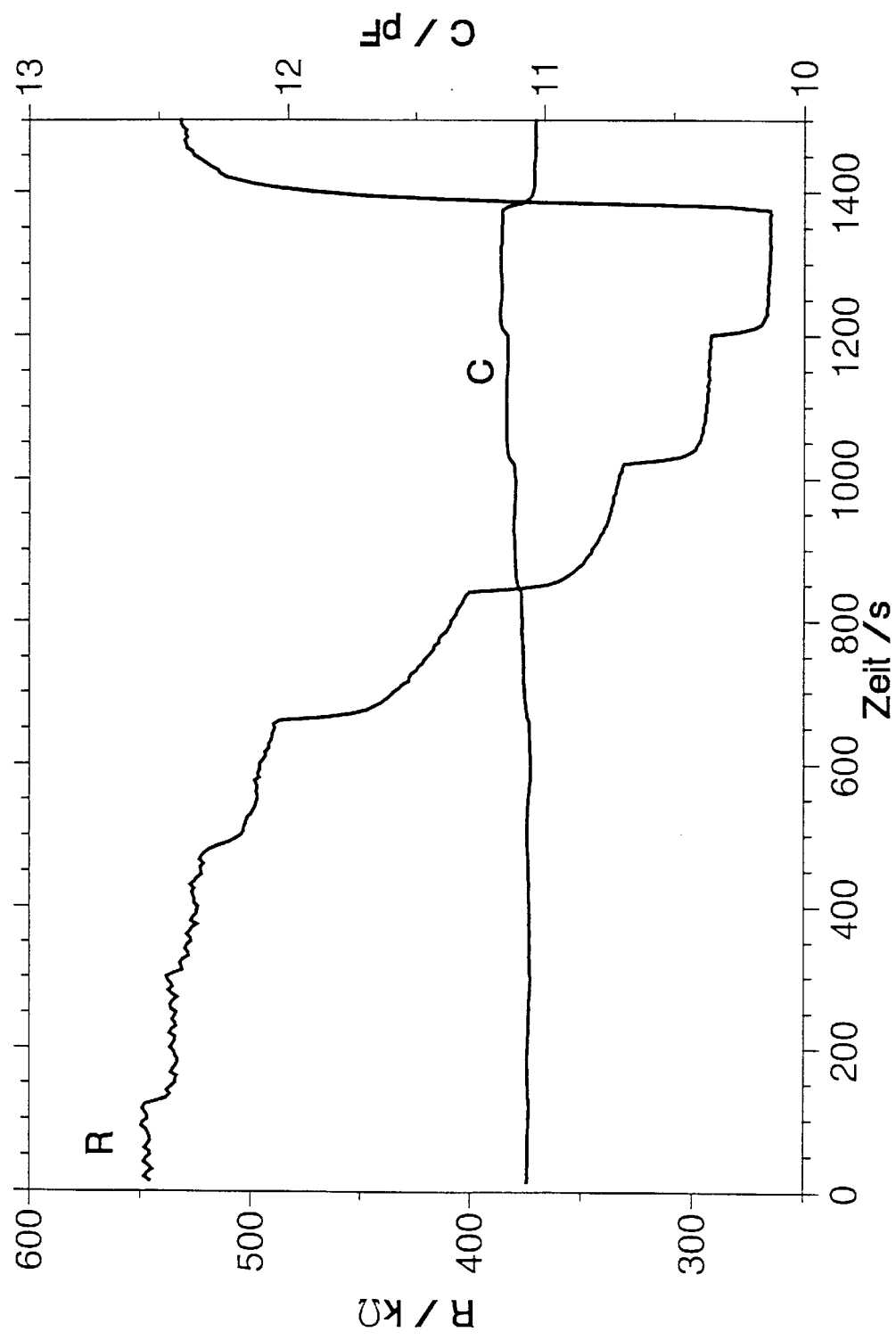
FIG. 8 measurement protocol, obtained with a substance sensor produced using the conventional thick layer technique, of which the finger breadth s=100 $\mu$m.
Figure 9:
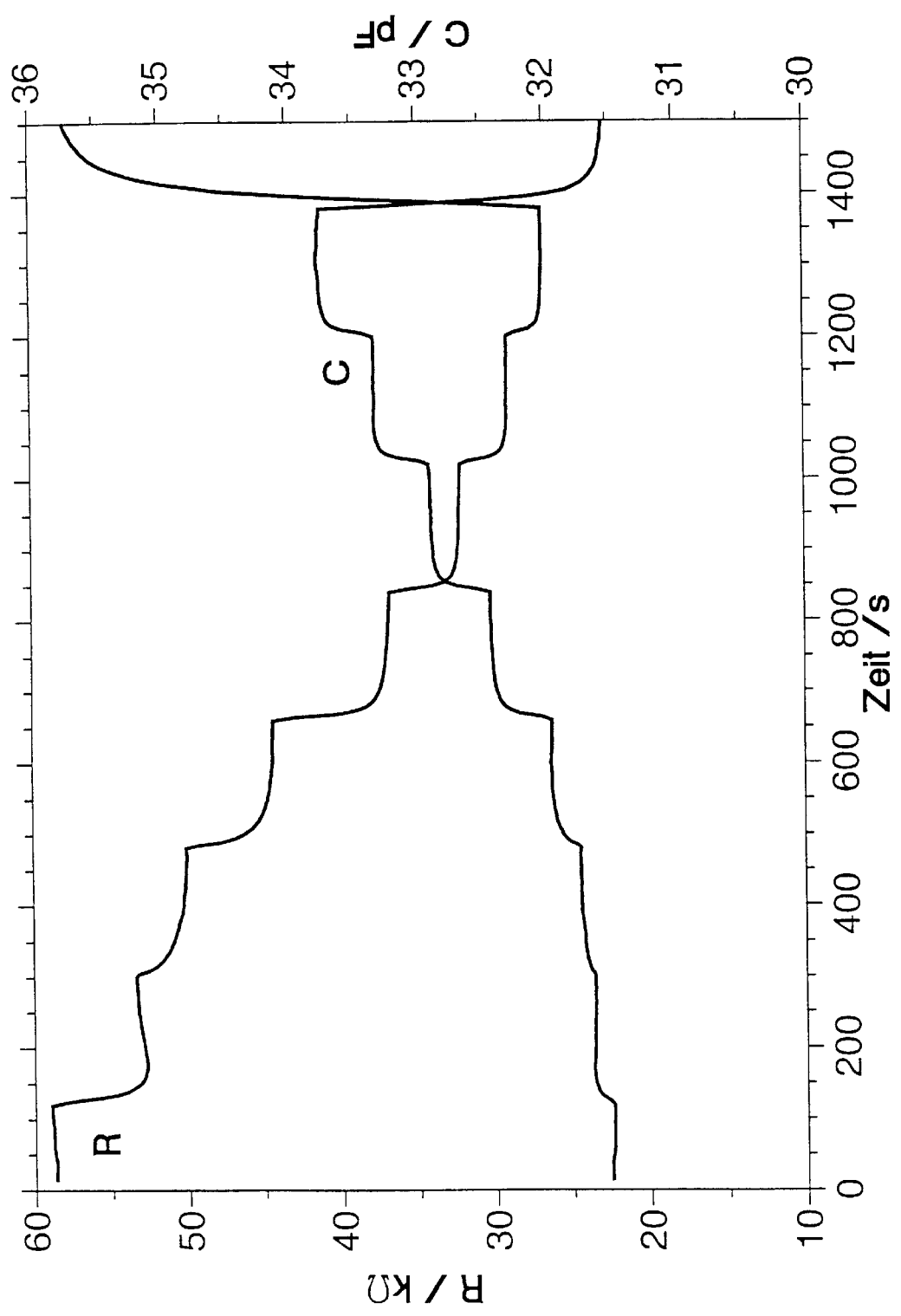
FIG. 9 measurement protocol, obtained using a substance sensor according to the invention, of which the finger breadth s=20 $\mu$m.

FIG. 7 through FIG. 9 shows a measurement protocol, which was obtained using various sensors. The sensors differ essentially in the structure breadth. The functional layer of all three sensors was prepared from the same zeolite batch according to the same manufacturing process. Illustrated is the sequence of the signal processor in a working temperature of the sensor upon exposure of the sensor to 5 ppm, 10 ppm, 20 ppm, 40 ppm, 60 ppm, 80 ppm, and 100 ppm ammonia in the atmosphere, which simulate the exhaust gas of an automobile. The measurement signals were recorded using an impedance measurement bridge using respectively the same frequency and evaluated as parallel circuit of a capacitor and a resistor (dissipative capacitor).

The sensor A (FIG. 7) exhibits a finger breadth of $s=10$ $\mu m$. Sensor A was produced using hybrid technology. The IDC structure of sensor A was produced using the thin layer technique and the zeolite layer was produced using the thick layer technique.

Sensor B (FIG. 8) exhibited a finger breadth of $s=100$ $\mu m$. Sensor B was completely produced using the conventional thick layer technique.

Sensor C (FIG. 9) exhibited a finger breadth of $s=20$ $\mu m$. Sensor C was completely produced in accordance with the invention following Steps 1 through 7.

It is readily apparent that the impedance of the Sensor A produced using expensive hybrid technology at 0 ppm ammonia lies at approximately 30 k$\Omega$, with changes of the impedance upon exposure to gas of 10 k$\Omega$. The capacity changed by approximately 1.5 pF at zero values by 83 pF. Such values of impedance in capacity are not economically measurable using conventional technology.

The impedance of the Sensor B, which is produced using the conventional thick layer technique, likewise exhibits changes about a factor of 1.5. However, the zero impedance is approximately 550 k$\Omega$ and is only measurable by a high ohm impedance analyzer. The capacity also can only be determined by expensive or complex means. Economical measurements cannot be carried out with the aid of this sensor type.

Sensor C produced in accordance with the invention exhibits an impedance change of approximately 30 k$\Omega$, with a zero impedance value of 60 k$\Omega$. The capacity changes by approximately 2 pF at a zero impedance of 30.5 pF. Such values of impedance in capacity are economically measurable with conventional technology.

In addition, in accordance with the product produced in accordance with the invention, a presently not understood effect can be observed which leads to a heightened sensitivity. While in the manufacture using a "pure" technique (thin layer technique or thick layer technique, Sensor A or B), the relationship of the impedance value of 0 ppm and 100 ppm ammonia corresponds to only about 1.5, one observes with the inventive sensor an impedance relationship of 2. In addition, the relative capacity change $\Delta C/C_0$ to be measured is greatest using the inventive Sensor type C at 6.3%. A possible explanation could lie in a further advantage of this process which by the improved aspect relationship A, that is in enlarged ratio or relationship of the thickness d of the electrode finger to the finger breadth b ($A_v=d/b$), increases the field lines in the functional layer. For comparison: with Sensor A, the aspect relationship $A_v=0.2$ $\mu m/10$ $\mu m=2\%$. With Sensor B, the aspect relationship was $A_v=8$ $\mu m/100$ $\mu m=8\%$. With Sensor C, the aspect relationship was $A_v=4$ $\mu m/20$ $\mu m=20\%$.

The described process can be employed for production of transducers for substance sensors with any of various functional layers. Its advantages are demonstrated above all when high ohm or capacitive functional layers are employed and produced using the thick layer technique. Thereby, it offers the benefit of the temperature stability of sensors which are produced in the thick layer technique, in combination with the structural resolution of sensors which are produced in accordance with the thin layer technique. Further, aspect relations can be achieved which retain the electrical field lines more in the functional layer. Therewith, the sensor signal in relationship to the zero impedance value is larger.

What is claimed is:

1. A high-temperature substance sensor produced by a process comprising:

providing a substrate (4) having an upper side and a lower side, providing on said lower side of said substrate (4) a device (6) for raising and maintaining the temperature of the sensor, providing on said upper side of said substrate (4), using a thick layer technique, an electrically conductive layer as a precursor of a capacitor structure (38), structuring the electrically conductive layer using a photolithographic structuring process comprising applying a photosensitive resin layer upon the electrically conductive layer, applying a photo mask, which corresponds to the capacitor structure, upon the resin layer, exposing the resin layer covered with the photo mask to light, removing the exposed areas of the resin layer, and removing the areas of the electrically conductive layer not covered by resin to produce an interdigitated capacitor structure (38) with a structure size smaller than 50 $\mu m$ and a thickness d greater than 4 $\mu m$, wherein in the interdigitated capacitor structure electrode fingers are interdigitated, and wherein the aspect ratio of the thickness of the electrode finger (d) to the finger breadth (b) is greater than 0.10, and providing a functional layer (18) upon said structured electrically conductive layer.

2. A high temperature substance sensor according to claim 1, wherein the capacitor structure (38) is comprised of a metal.

3. A high temperature substance sensor according to claim 2, wherein said metal is selected from the group consisting of gold and platinum.

4. A high temperature substance sensor according to claim 1, wherein said substance sensor is a gas sensor, and wherein said functional layer is a layer of which the electrical impedance changes upon exposure to a gas.

5. A high-temperature substance sensor produced by a process comprising:

provided a substrate (4) having an upper side and a lower side, providing on said lower side of said substrate (4) a device (6) for raising and maintaining the temperature of the sensor, providing on said upper side of said substrate (4), using a thick layer technique, an electrically conductive layer as a precursor of a capacitor structure (38), structuring the electrically conductive layer using a photolithographic structuring process comprising: applying a photosensitive resin layer upon the electrically conductive layer, applying a photo mask, which corresponds to the negative of the capacitor structure, upon the resin layer, exposing the photo mask covered resin layer to light, removing of the unexposed areas of the resin layer, and removing the areas of the electrically conductive layer not covered by resin to produce an interdigitated capacitor structure (38) with a structure size smaller than 50 $\mu$m and a thickness d greater than 4 $\mu$m, wherein in the interdigitated capacitor structure electrode fingers are interdigitated, and wherein the aspect ratio of the thickness of the electrode finger (d) to the finger breadth (b) is greater than 0.10, and providing a functional layer (18) upon said structured electrically conductive layer.

* * * * *